United States Patent [19]

Sun

[11] Patent Number: 5,072,066
[45] Date of Patent: Dec. 10, 1991

[54] INHIBITING POPCORN POLYMER FORMATION WITH ESTERS OF INORGANIC ACIDS

[75] Inventor: Hsiang-ning Sun, Houston, Tex.

[73] Assignee: Exxon Chemical Patents Inc., Linden, N.J.

[21] Appl. No.: 647,359

[22] Filed: Jan. 29, 1991

[51] Int. Cl.$^5$ ............................ C07C 7/20; B08B 9/00
[52] U.S. Cl. ...................................... 585/2; 134/22.19; 585/3; 585/950
[58] Field of Search .............................. 585/2, 3, 950; 134/22.19

[56] References Cited

U.S. PATENT DOCUMENTS

| | | | |
|---|---|---|---|
| 2,947,795 | 8/1960 | Keown | 585/4 |
| 3,148,225 | 9/1964 | Albert | 585/4 |
| 3,175,012 | 3/1965 | Colbert | 570/104 |
| 3,265,751 | 8/1966 | McCoy et al. | 585/4 |
| 3,265,752 | 8/1966 | Whiton et al. | 585/4 |
| 3,493,603 | 2/1970 | Albert et al. | 560/70 |
| 3,560,577 | 2/1971 | Benjamins | 568/949 |
| 4,404,413 | 9/1983 | Haskell | 585/2 |
| 4,941,926 | 7/1990 | Nakajima | 585/5 |
| 4,956,020 | 9/1990 | Nakajima | 585/5 |

FOREIGN PATENT DOCUMENTS

63/223003 9/1988 Japan .

OTHER PUBLICATIONS

Liu, Plugging-up of Equipment by Self-Polymerization Butadiene Production and its Prevention, China Synthetic Rubber Industry, 11(5) 357–360 (1988).

Liu et al., Determination of Traces of Diethylhydroxylamine Inhibitor in C5 Fraction by Gas Chromatography, China Synthetic Rubber Industry, 12(6), 408–410 (1989).

Primary Examiner—Curtis R. Davis
Attorney, Agent, or Firm—Linda K. Russell

[57] ABSTRACT

Inhibition of popcorn polymer growth by treatment with an inorganic acid ester. This compound can be admixed with organic material from which popcorn polymer is formed, or added to a system for the recovery, use or storage of such organic material.

16 Claims, No Drawings

INHIBITING POPCORN POLYMER FORMATION WITH ESTERS OF INORGANIC ACIDS

CONCURRENTLY FILED APPLICATIONS

Concurrently with this application, also filed were applications entitled METHOD FOR INHIBITING POPCORN POLYMER FORMATION BY HEAT, Ser. No. 07/647,365 filed Jan. 29, 1991; INHIBITING POPCORN POLYMER FORMATION WITH SULFUR-CONTAINING COMPOUNDS, Ser. No. 07/647,356 filed Jan. 29, 1991; INHIBITING POPCORN POLYMER FORMATION WITH COMPOUNDS INCORPORATING GROUP IV ELEMENTS, Ser. No. 07/647,357, filed Jan. 29, 1991; and INHIBITING POPCORN POLYMER FORMATION WITH ALKYL HALIDES, Ser. No. 07/647,358, filed Jan. 29, 1991. These applications are all incorporated herein in their entireties, by reference thereto.

BACKGROUND OF THE INVENTION

1. Field of the Invention

The present invention is directed to inhibiting or preventing popcorn polymer growth or formation, particularly such growth or formation in organic material. The desired result is effected by treatment with one or more esters of inorganic acids. This treatment is conducted with an amount of such inhibitor sufficient to prevent, inhibit, retard, or stop popcorn polymer growth.

2. Description of Background and Other Information

Popcorn polymers are known to form from all manner of organic material, particularly olefinically unsaturated monomers, including olefins and diolefins; especially susceptible are the conjugated diolefins, e.g., butadiene and isoprene, and vinyl compounds, e.g., styrenes and acrylates. Known as popcorn polymers because they resemble popped corn, these polymers are also referred to in the art as sponge polymers, granular polymers, cauliflower-like polymers, nodular polymers, fluffy polymers, proliferous polymers, and crusty polymers.

Popcorn polymer has been considered to occur from spontaneous monomer polymerization. It can occur in both liquid phase and vapor phase, and at any stage of use or handling of the monomer, e.g., recovery, separation, manufacturing, purification, storage, etc. High concentrations of monomer are particularly advantageous for its formation.

Specifically, it appears that the presence of one or more initiators—e.g., water, oxygen, hydrogen peroxide—results in the formation of popcorn polymer "seeds" in the organic material. The seeds themselves then perpetuate polymerization, without further requiring an initiator and/or a crosslinking agent; they serve as sites for further polymerization.

As the particular mechanism, it is believed that monomer diffuses through the surface of the growing polymer mass, and is added to the polymer at the center thereof. For this reason, such polymerization is referred to as occurring "from the inside out."

Consequently, there is continued incorporation of monomer into the polymer phase, leading to buildup of the popcorn polymer. The result is a hard polymeric foulant, which can cause serious equipment and safety concerns if left unchecked.

A particular problem attendant upon popcorn polymer formation is its extreme resistance to deactivation, once present in a system. Some of the seeds become attached to the processing and handling equipment, and cannot be readily removed by mechanical means; moreover, being insoluble in most common solvents, they are virtually impossible to wash out by use of such solvents.

Even after equipment and storage facilities have been cleaned thoroughly, residual particles of popcorn polymer remain, and promote unwanted polymer growth. Trace particles remaining in the equipment will stay active for long periods without the presence of monomer, and serve to initiate polymerization when once again contacted therewith.

Different inhibitors are known for use against popcorn polymer formation. Examples of these are the following: t-butylcatechol; sodium nitrite, as disclosed in LIU, "Plugging-Up of Equipment by Self-Polymerization Butadiene Production and Its Prevention," China Synthetic Rubber Industry, 11(5) 357–360 (1988); carbon disulfide and elemental phosphorous, as disclosed in HASKELL, U.S. Pat. No. 4,404,413, which also refers to hydrogen sulfide, to ethane-, propane-, and hexanethiol, and to ethyl disulfide as being known in the prior art; N,N-dialkylhydroxylamines, as disclosed in TOKAI ELECTRO-CHEMICAL CO., Japanese Kokai No. 66,223,003, as well as in LIU et al., "Determination of Traces of Diethylhydroxylamine Inhibitor in $C_5$ Fraction by Gas Chromatography," China Synthetic Rubber Industry, 12(6), 408–410 (1989), and in ALBERT, U.S. Pat. No. 3,148,225, the latter of these also referring to nitrites, nitroso compounds, $NO_2$, $N_2O_3$, phenolic compounds, sulfur, aromatic amines, and hydroxylamine as being known in the prior art; trialkylamine oxides, as also disclosed in TOKAI ELECTRO-CHEMICAL CO.; N-hydroxymorpholine, used in conjunction with N,N-dialkylhydroxylamines, as disclosed in WHITON et al., U.S. Pat. No. 3,265,752, or in conjunction with N-hydroxypiperidine, as disclosed in McCOY et al., U.S. Pat. No. 3,265,751; adducts of phenols and hydroxylamines, as disclosed in ALBERT et al., U.S. Pat. No. 3,493,063; reaction products of nitrous acid and 1,3-dichlorobutene-2 or diisobutylene, as disclosed in BENJAMINS, U.S. Pat. No. 3,560,577, which also refers to nitrogen dioxide, the addition product of 1,3-dichloro-2-butene and nitrogen dioxide, and ion-exchange resin containing nitrite ions, as being known in the prior art; butyraldoxime, as disclosed in KEOWN, U.S. Pat. No 2,947,795; and nitrogen tetroxide-diisobutylene addition products, as disclosed in COLBERT, U.S. Pat. No. 3,175,012.

Those inhibitors known in the prior art are generally effective in stopping the formation of popcorn polymer seeds. However, they are only minimally effective in stopping the growth of seeds already in existence. Further, such inhibitors which are relatively heavy will work in liquid phase, but are of little or no use in vapor phase, because in this state their weight hinders their distribution.

It has been discovered that esters of inorganic acids will inhibit popcorn polymer formation. Specifically, such compounds are characterized by at least one substituted or nonsubstituted hydrocarbyl group and the anionic moiety of an inorganic acid.

For instance, inhibitors of the invention can be used to treat organic material wherein such popcorn polymer formation occurs. Specifically, these inorganic acid esters may be admixed with, or added to, such organic material during the use, handling, or storage thereof.

SUMMARY OF THE INVENTION

According to the invention, inhibition of popcorn polymer growth is effected with an inhibitor comprising at least one inorganic acid ester. Included within the scope of the invention are the inorganic acid esters having the formula:

$$H_aXR_b$$

wherein
X is an inorganic acid anionic moiety,
$a \geq 0$,
$b \geq 1$,
$a+b$ = the charge of the inorganic acid anionic moiety, and
R is selected from the group consisting of substituted and nonsubstituted hydrocarbyl groups, whereby these groups may be the same or different where $b > 1$.

Preferably X is selected from the group consisting of $SO_4$, $SO_3$, $PO_4$, $PO_3$, $CO_3$, $BO_3$, and $SiO_4$. Also as a preferred embodiment, R is selected from the group consisting of $C_{1-10}$ alkyl and phenyl.

Suitable inorganic acid esters of the invention include dimethyl sulfate, diethyl sulfate, dimethyl sulfite, triphenyl phosphate, trimethyl phosphite, dimethyl carbonate, trimethyl borate, tetramethyl silicate, and tetraethyl silicate. Dimethyl sulfate and trimethyl phosphite are particularly preferred.

The process of the invention employs an amount of inhibitor sufficient to inhibit popcorn polymer growth. As an aspect of the process, the inhibitor is added to a system for organic material from which popcorn polymer is formed.

Preferably, the popcorn polymer-forming material comprises at least one vinyl compound. More preferably, this at least one vinyl compound comprises at least one divinyl compound.

In a particularly preferred embodiment of the process of the invention, the organic material itself is treated with at least one inorganic acid ester—preferably, in an amount sufficient to inhibit popcorn polymer formation. Such inorganic acid ester can be added to the organic material continuously, or intermittently, particularly where such organic material is provided as a moving stream.

As a suitable concentration, 0.5-100,000 wppm of the inhibitor is added to the organic material. Preferably, the concentration is 1-5000 wppm; more preferably, the concentration is 5-1500 wppm.

DESCRIPTION OF PREFERRED EMBODIMENTS

The inhibitor compounds of the invention are those esters of inorganic acids which inhibit popcorn polymer formation, e.g., in organic material from which popcorn polymer is formed. These compounds are also referred to herein by the term "inorganic acid esters".

The term "inhibit" is understood as referring to all degrees of adversely affecting the formulation of popcorn polymer. Completely halting popcorn polymer growth is included, as well as slowing such growth.

The inorganic acid esters of the invention include the anionic moiety of the corresponding inorganic acids, with one or more hydrocarbyl groups in place of hydrogen. Suitable such inhibitor compounds are those of the formula:

$$H_aXR_b$$

wherein
X is an inorganic acid anionic moiety,
$a \geq 0$,
$b \geq 1$,
$a+b$ = the charge of the inorganic acid anionic moiety, and
R is selected from the group consisting of substituted and nonsubstituted hydrocarbyl groups, whereby these groups may be the same or different where $b > 1$.

Suitable such substituted and nonsubstituted hydrocarbyl groups include aliphatic and aromatic groups. Preferred aliphatic groups are the $C_{1-10}$ alkyls, with methyl and ethyl being particularly preferred. The preferred aromatic group is phenyl.

Encompassed within the scope of this invention are the esters of sulfuric, sulfurous, phosphoric, phosphorous, carbonic, and boric acids. Also suitable are the esters of silicic acids, particularly orthosilicic acid. Particular inhibitors of the invention include dimethyl sulfate, diethyl sulfate, dimethyl sulfite, triphenyl phosphate, trimethyl phosphite, dimethyl carbonate, trimethyl borate, tetramethyl silicate, and tetraethyl silicate.

The inorganic ester inhibitors of the invention are generally liquid at ambient conditions. This feature facilitates their ease of handling, particularly for the purposes as discussed herein.

The inhibitor compounds of the invention are for use with organic material; the term "organic material" encompasses all organic material wherein, or from which, popcorn polymer forms. Such organic material includes, but is not limited to, olefins and diolefins, particularly the conjugated diolefins, as well as the vinyl compounds, as discussed in HASKELL, U.S. Pat. No. 4,404,413; this patent is incorporated herein in its entirety, by reference thereto.

Specifically, suitable such organic material includes monovinyl compounds such as styrene, acrylic acid and its esters, such as methyl acrylate, ethyl acrylate, and butyl acrylate; methacrylates such as methyl methacrylate, ketones such as methyl vinyl ketone, and nitriles such as acrylonitrile. Appropriate divinyl compounds include 1,3-butadiene, isoprene, dimethyl-2,3-buta-1,3-diene, chloroprene, and bromoprene.

Further as to the organic material, two or more monomers, such as any combination of those discussed above, as well as popcorn polymer sources or seeds formed from any such combination, may also be treated with the inhibitor of the invention.

While retaining its ordinary meaning in the art, i.e., as the starting unit for polymerization, the term "monomer", as used herein, is understood to encompass all organic material suitable for treatment with the inorganic acid esters of the invention. It is further understood as encompassing all such organic material wherein is formed the popcorn polymer whose growth or formation is to be inhibited.

The invention pertains to any process utilizing at least one inorganic acid ester for inhibiting popcorn polymer growth or formation. Particularly, the invention encompasses treatment of monomer with the at least one inorganic acid ester to inhibit, prevent, retard, or stop formation or growth of popcorn polymer.

For example, monomer can be contacted with the inorganic acid ester inhibitor, e.g., with the inhibitor being admixed therewith, or added thereto. As an advantage for use in this manner, the inorganic acid esters of the invention are effective as inhibitors in both the liquid and vapor phases.

The inhibitors of the invention are suitable for treatment of monomer in all stages and steps of recovery, manufacture, use, storage, or any other type of handling thereof. For instance, these inhibitors may be used in processes for separating desired monomer from a mixed hydrocarbon stream, and in processes involving chemical reaction of the monomer; they may also be added to the monomer retained in storage tanks.

The treatment may be effected by any appropriate means. Preferably, inorganic acid ester is added to the monomer in such a manner as to be dispensed therethrough, and thereby provide optimal protection against popcorn polymer formation.

For instance, inhibitor can be added to the monomer continuously, or, in contrast, intermittently, particularly where the monomer is provided as a flowing stream. The results to be obtained from continuous and intermittent addition of inhibitor are not necessarily the same; different advantages and disadvantages appear to be attendant upon each such manner of addition.

Continuous addition of inhibitor tends to maintain prevention of seed formation, and is therefore advantageous in combatting any appearance of popcorn polymer. However, it requires that a greater amount of inhibitor be used, and is correspondingly more expensive.

Intermittent addition of inhibitor, involving the addition of discrete portions of inhibitor into the organic material at spaced intervals, will, upon each such admission of the inhibitor, "kill" whatever seeds have formed during the interval between additions, i.e., prevent their further growth, or at least retard such growth. Because such addition is not continuous, it requires less of the inhibitor than is employed in continuous addition, and is correspondingly cheaper; however, it tends to allow the growth of new seeds during the periods of time between additions of inhibitor.

The amount of inhibitor to be used will vary according to different factors, including: how readily popcorn polymer formation occurs in the monomer or monomers being treated; the growth rate of such popcorn polymer once polymerization thereof has been initiated; and, if popcorn polymer formation has already begun, the size and number of seeds present. Concentrations of between about 0.5 wppm and about 100,000 wppm of inhibitor in the monomer are suitable, with a more preferred range being between about 1 wppm and about 5000 wppm; the most preferred range is between about 5 and about 1500 wppm.

Particularly as to intermittent addition, additional factors to be considered in practicing this aspect of the invention, beside the above-discussed addition rate of inhibitor, include: how long each addition should be maintained (i.e., how much inhibitor should be included in each discrete amount added to the monomer); how much time should elapse between such additions of inhibitor; how many such additions should be employed. All factors pertaining to both continuous and intermittent addition may be readily ascertained and determined by one of ordinary skill in the art, to achieve the desired results pertaining to inhibition of popcorn polymer formation.

Treatment of monomer with inorganic acid ester inhibitor of the invention can act against popcorn polymer in different ways. Such application will prevent, or at least retard, formation of popcorn polymer. It will also kill, or at least slow the growth of, popcorn polymer with which it comes into contact, e.g., seeds or deposits in the systems wherein monomer is recovered, used, or stored.

The following experimental procedure demonstrates the utility of the inhibitors of the invention for inhibiting popcorn polymer formation; specifically, two representative examples of such inhibitors are tested. This procedure is included, not as limiting the invention presented herein, but rather, to be illustrative thereof.

EXPERIMENTAL PROCEDURE

This experimental procedure involved exposure of popcorn polymer seeds, derived from different monomers, to different inorganic acid ester inhibitors of the invention; with each seed, such exposure was conducted in the presence of the monomer from which the seed was formed. As a control, this procedure also included a 1,3-butadiene seed/monomer system without the presence of such inhibitor.

Specifically, in each instance, all air was removed from a glass polymerization vessel, either by evacuation, or by flushing with nitrogen. The monomer was then either condensed into the vessel at $-78°$ C., or added thereto by syringe, depending upon whether it is liquid or gaseous at room temperature, and upon atmospheric pressure. Specifically, the butadiene was added by the condensation procedure; isoprene and 2,3-dimethyl 1,3-butadiene, by syringe.

Where inhibitor was used, a particular proportion thereof, calculated according to the amount of monomer used, was added to the vessel. Dimethyl sulfate and trimethyl phosphite, the two inhibitors tested in this procedure, being liquid at room temperature, were both added by syringe. As previously indicated, no inhibitor was used for the control.

A popcorn polymer seed (formed, as stated, from the same monomer providing the environment in the vessel) was placed on the bottom of the vessel for those tests utilizing liquid phase polymerization (i.e., maintaining the seed in the liquid phase). For tests utilizing gas phase polymerization (i.e., maintaining the seed in the gas phase), the seed was suspended in the vessel, so as not to be in contact with liquid therein.

In each test, the system thus established was maintained at a specified temperature, as a static system, and at autogenic pressure. Popcorn polymer growth rates were measured according to the growth rate of the 1,3-butadiene control.

Specifically, the amount of growth obtained from the butadiene control was arbitrarily designated as 1.0. Growth of all the other seeds was measured according to this standard.

The results of this procedure are set forth in the Table below.

TABLE

| Monomer | Inhibitor Conc. (wppm) | Polymer | Popcorn Seed Medium | Treatment Period (Days) | Temperature | Treatment (°C.) | Growth | Rate |
|---|---|---|---|---|---|---|---|---|
| butadiene | Control (no inhibitor) | (V) | | 14 | | 60 | | 1.0 |
| butadiene | DMS/1000 | | (V) | 14 | | 60 | | 0 |
| butadiene | DMS/1000 | | (L) | 14 | | 60 | | 0 |
| butadiene | TMP/1000 | | (V) | 21 | | 60 | | 0.32 |
| butadiene | TMP/1000 | | (V) | 21 | | 60 | | 0.26 |
| 2,3-DMB | DMS/1000 | | (V) | 21 | | 25 | | 0.42 |
| 2,3-DMB | DMS/1000 | | (V) | 21 | | 25 | | 0.35 |

DMS—dimethyl sulfate
TMP—trimethyl phosphate
2,3 DMB—2,3-dimethyl 1,3-butadiene

These tests demonstrate the considerable inhibitory effect which the inorganic acid esters of the invention have upon popcorn polymer growth. No growth was observed in either the vapor phase or liquid phase butadiene/DMS systems. The other dimethyl sulfate systems, and the trimethyl phosphate systems, exhibited less growth than the control, even though the treatment period for the control was only two thirds as long as that of the systems including inorganic acid ester inhibitor.

Finally, although the invention has, as been noted above, been described with reference to particular means, materials and embodiments, it should be noted that the invention is not limited to the particulars disclosed, and extends to all equivalents within the scope of the claims.

What is claimed is:

1. A method for inhibiting popcorn polymer growth in a system for organic material from which said popcorn polymer is formed, comprising addition, to said system, of at least one inorganic acid ester having the formula $$H_a X R_b$$

wherein
X is an inorganic acid anionic moiety,
$a \geq 0$,
$b \geq 1$,
$a+b$ = the charge of the inorganic acid anionic moiety, and
R is selected from the group consisting of substituted and nonsubstituted hydrocarbyl groups, whereby these groups may be the same or different where $b > 1$.

2. The method of claim 1, wherein X is selected from the group consisting of $SO_4$, $SO_3$, $PO_4$, $PO_3$, $CO_3$, $BO_3$, and $SiO_4$.

3. The method of claim 2, wherein R is selected from the group consisting of $C_{1-10}$ alkyl and phenyl.

4. The method of claim 3, wherein said at least one inorganic acid ester is selected from the group consisting of dimethyl sulfate, diethyl sulfate, dimethyl sulfite, triphenyl phosphate, trimethyl phosphite, dimethyl carbonate, trimethyl borate, tetramethyl silicate, and tetraethyl silicate.

5. The method of claim 1, wherein said organic material comprises at least one vinyl compound.

6. The method of claim 5, wherein said at least one vinyl compound comprises at least one divinyl compound.

7. A method for inhibiting popcorn polymer growth in organic material, comprising treatment of said organic material with at least one inorganic acid ester having the formula $$H_a X R_b$$

wherein
X is an inorganic acid anionic moiety,
$a \geq 0$,
$b \geq 1$,
$a+b$ = the charge of the inorganic acid anionic moiety, and
R is selected from the group consisting of substituted and nonsubstituted hydrocarbyl groups, whereby these groups may be the same or different where $b > 1$.

8. The method of claim 7, wherein X is selected from the group consisting of $SO_4$, $SO_3$, $PO_4$, $PO_3$, $CO_3$, $BO_3$, and $SiO_4$.

9. The method of claim 8, wherein R is selected from the group consisting of $C_{1-10}$ alkyl and phenyl.

10. The method of claim 9, wherein said at least one inorganic acid ester is selected from the group consisting of dimethyl sulfite, triphenyl phosphate, trimethyl phosphite, dimethyl carbonate, trimethyl borate, tetramethyl silicate, and tetraethyl silicate.

11. The method of claim 7, wherein the concentration of said at least one inorganic acid ester employed in said treatment is from about 0.5 to about 100,000 wppm of said organic material.

12. The method of claim 11, wherein the concentration of said at least one inorganic acid ester employed in said treatment is from about 5 to about 1500 wppm of said organic material.

13. The method of claim 7, wherein said organic material comprises at least one vinyl compound.

14. The method of claim 13, wherein said at least one vinyl compound comprises at least one divinyl compound.

15. The method of claim 7, wherein said treatment comprises continuous addition of said at least one inorganic acid ester to said organic material.

16. The method of claim 7, wherein said treatment comprises intermittent addition of said at least one inorganic acid ester to said organic material.

* * * * *